United States Patent
Munnig et al.

(10) Patent No.: US 8,357,827 B2
(45) Date of Patent: Jan. 22, 2013

(54) PROCESS FOR THE CONTINUOUS PREPARATION OF NITROBENZENE

(75) Inventors: Jurgen Munnig, Kaarst (DE); Bernd Pennemann, Bergisch Gladbach (DE); Andreas Karl Rausch, Neuss (DE)

(73) Assignee: Bayer MaterialScience AG, Leverkusen (DE)

( * ) Notice: Subject to any disclaimer, the term of this patent is extended or adjusted under 35 U.S.C. 154(b) by 36 days.

(21) Appl. No.: 13/019,350

(22) Filed: Feb. 2, 2011

(65) Prior Publication Data

US 2011/0196177 A1     Aug. 11, 2011

(30) Foreign Application Priority Data

Feb. 5, 2010    (DE) .......................... 10 2010 006 984

(51) Int. Cl.
*C07C 205/00*     (2006.01)

(52) U.S. Cl. ........................................ 568/939; 568/927

(58) Field of Classification Search ........................ None
See application file for complete search history.

(56) References Cited

U.S. PATENT DOCUMENTS

| | | | |
|---|---|---|---|
| 2,256,999 | A | 9/1941 | Castner |
| 4,091,042 | A | 5/1978 | Alexanderson et al. |
| 5,616,818 | A | 4/1997 | Pirkl et al. |
| 5,763,697 | A | 6/1998 | Hermann et al. |
| 6,562,247 | B2 | 5/2003 | Gillis et al. |
| 7,326,816 | B2 | 2/2008 | Knauf et al. |
| 7,781,624 | B2 | 8/2010 | Rausch et al. |
| 2003/0055300 | A1* | 3/2003 | Chrisochoou et al. ........ 568/937 |
| 2009/0187051 | A1* | 7/2009 | Rausch et al. ................ 568/939 |

FOREIGN PATENT DOCUMENTS

| | | |
|---|---|---|
| EP | 0373966 B1 | 10/1993 |
| EP | 0489211 B1 | 2/1996 |
| EP | 0436443 B1 | 4/1996 |
| EP | 0779270 B1 | 6/2000 |

* cited by examiner

*Primary Examiner* — Sudhakar Katakam
(74) *Attorney, Agent, or Firm* — Lyndanne M. Whalen; N. Denise Brown

(57) ABSTRACT

Nitrobenzene is continuously produced by nitration of benzene with mixed acid under adiabatic conditions. In this process, the pressure upstream of the nitration reactor is from 14 bar to 40 bar above the pressure in the gas phase of the phase separation apparatus used to separate crude nitrobenzene and waste acid.

5 Claims, No Drawings

PROCESS FOR THE CONTINUOUS PREPARATION OF NITROBENZENE

BACKGROUND OF THE INVENTION

The present invention relates to a process for the continuous preparation of nitrobenzene by nitration of benzene with mixed acid. In this process, the pressure upstream of the nitration reactor is from 14 bar to 40 bar above the pressure in the gas phase of a phase separation apparatus for separating crude nitrobenzene and waste acid.

The continuous process for the preparation of nitrobenzene of the present invention is based upon the concept of adiabatic nitration of benzene with a mixture of sulfuric acid and nitric acid (so-called "mixed acid"). An adiabatic nitration process was claimed for the first time in U.S. Pat. No. 2,256,999. More current embodiments of an adiabatic nitration process are described, for example, in EP 0 436 443 B1; EP 0 771 783 B1; and U.S. Pat. No. 6,562,247 B2. Processes in which the reaction is carried out adiabatically are distinguished by the fact that no technical measures are taken to supply heat to the reaction mixture or to remove heat from the reaction mixture.

A common feature of the known adiabatic processes is that the benzene and nitric acid starting materials are reacted in the presence of a large excess of sulfuric acid. The sulfuric acid takes up the heat of reaction that is liberated and the water formed in the reaction.

In order to carry out the reaction, nitric acid and sulfuric acid are generally mixed to form the so-called mixed acid (also called nitrating acid), and benzene is metered into the mixed acid. The product obtained reacts with the nitric acid or with "nitronium ions" formed in the mixed acid substantially to form water and nitrobenzene. Benzene is used in at least the stoichiometric amount—based on the molar amount of nitric acid—but preferably in a 2% to 10% excess compared with the stoichiometrically required amount of benzene.

The most important criterion for describing the quality of an adiabatic process for the nitration of aromatic hydrocarbons is the content of undesirable by-products in the product. Such by-products are formed by repeated nitration or oxidation of the aromatic hydrocarbon or of the nitroaromatic compound. In nitration of benzene, the content of dinitrobenzene and of nitrophenols, in particular trinitrophenol (picric acid), which is rated as explosive, is always discussed.

In order to obtain nitrobenzene with particularly high selectivity, the nature of the mixed acid to be used has been specified in detail. (See, e.g., EP 0 373 966 B1; EP 0 436 443 B1; and EP 0 771 783 B1). It has been noted that the content of by-products is determined by the maximum temperature attained by the reaction mixture (EP 0 436 443 B1, column 15, l. 22-25). It is also known that a high initial conversion is advantageous for high selectivity, and that this high initial conversion may be achieved with optimal mixing at the beginning of the reaction (EP 0 771 783 B1, paragraph [0014]).

The inexpensive and efficient configuration of the initial mixing (dispersion) and the repeated mixing (re-dispersion) of aromatic compounds in the mixed acid is the subject of numerous studies. As a result, use of mixing nozzles (EP 0 373 966 B1; EP 0 771 783 B1) and specially formed static dispersing elements (EP 0 489 211 B1; EP 0 779 270 B1; EP 1 291 078 A1; and U.S. Pat. No. 6,562,247 B2) has been proposed. It is also possible to combine the two concepts.

If static mixing elements (dispersing elements) are used for the mixing, the pressure loss at these static mixing elements is critical for the quality of the mixing. The pressure upstream of the reactor must be at least equal to the sum of the pressure losses of all the dispersing elements in the reactor. Other factors may also have to be taken into account. Such factors include the static pressure of the liquid column in the reactor and the pressure in the phase separation apparatus. Within the scope of this invention, "pressure upstream of the reactor" is understood as being the absolute pressure that the liquid starting materials are under immediately before and also on entry into the reactor.

According to the teaching of the prior art, the total pressure loss over the reactor and, where appropriate, further apparatuses connected downstream of the reactor (and accordingly also the pressure upstream of the reactor) is to be kept as low as possible. See, for example, EP 1 291 078 A2, paragraph [0017]. Another example is described in EP 2 070 907 A1, where it is disclosed that an increase in the absolute pressure upstream of the reactor from 13.5 bar to 14.5 bar as a result of deposits of metal sulfates in the dispersing elements leads to a reduction of about 18% in the throughput of sulfuric acid (Example 1). The prior art therefore teaches that high pressure losses, and accordingly, high absolute pressures, upstream of the reactor are to be avoided.

An example of the mixing of aromatic compound and mixed acid by means of a suitable nozzle without static dispersing elements is found in EP 0 373 966 B1. Here, a range of from 0.689 bar to 13.79 bar is given as a suitable range for the working pressure. "Back pressure" equals counter-pressure in the nozzle, i.e., the pressure of the liquid starting material stream (aromatic compound or mixed acid) on entry into the reactor, which is equivalent to the pressure of the starting material stream in question upstream of the reactor. (p. 5, l. 12 to 13) This disclosure also teaches that, under normal conditions, a pressure higher than 11.03 bar is not expected to be necessary (p. 5, l. 15 to 16).

The possible lower limit for the pressure upstream of the reactor is additionally established by the fact that the benzene should be in liquid form at the reactor inlet under the given conditions (U.S. Pat. No. 4,091,042, column 2, lines 14 to 17). Regarding the possible upper limit, it is to be noted that, according to the prior art, the pressure loss per static dispersing element is kept as low as possible because, in order to overcome a higher pressure loss, for example, a pump having a higher power is required, which in turn leads to higher costs for the process as a whole (EP 1 291 078 A2, paragraph [0017]). Also, attempts are generally made to keep the number and thickness (stability) of the dispersing elements preferably as low as possible and thus minimize the cost of the dispersing elements which are often produced from special tantalum material. (EP 1 291 078 A1, paragraph [0018])

The pressure inside the reactor is also limited by the material used to construct the tubular reactor. Under generally conventional conditions for the adiabatic nitration of benzene at from 80° C. to 150° C. using sulfuric acid having a concentration of from 65% by mass to 80% by mass, only tantalum, Teflon and glass are permanently resistant. High-alloy steels can likewise be used, in particular when the sulfuric acid always contains a residual amount of nitric acid, becaue nitric acid has a passivating effect on the high-alloy steel. On an industrial scale, steel pipes enamelled with glass are especially used for the adiabatic nitration of benzene. Steel enamel pipe segments are to be manufactured in accordance with DIN standard 2873 of June 2002 for nominal pressure level PN10 and at most for nominal pressure level PN25. Nominal pressure level PN25 is permissible only in the case of pipe diameters up to a nominal width of DN150 (nominal pressure levels according to EN1333, nominal width according to DIN EN ISO 6708). As is known to the person skilled in the art, the permissible operating pressure is not identical to the nominal pressure level but must be calculated in view of the temperature and material being used. At higher temperatures, the permissible operating pressure is correspondingly lower due to the reduction in the permissible material parameters. In the construction of chemical installations, fittings (valves, slides, etc.) are required in addition to apparatuses and pipes, which fittings are in turn subject to their own standards. The result of these high requirements is that the skilled person building large-scale nitration installations must be concerned with keeping the pressure within the installation, particularly the pressure upstream of the reactor, low, as long as he/she does not know that a significant advantage is obtained thereby.

Although processes described in the prior art permit the preparation of a crude nitrobenzene which has a low content of by-products, i.e., from 100 ppm to 300 ppm dinitrobenzene and from 1500 ppm to 2500 ppm nitrophenols of which picric acid can account for from 10% by mass to 50% by mass of the nitrophenols, a critically important factor for industrial production, apart from the purity of the crude nitrobenzene, is that the preparation of the nitroaromatic compounds be carried out in reaction devices that are as compact as possible. This is a particular concern in view of the constantly rising demand for nitroaromatic compounds, especially for the preparation of aromatic amines and aromatic isocyanates.

An important parameter for describing the relationship between the amount of product that can be produced and the size of the reaction device is the space-time yield (STY). STY is calculated as the quotient of the amount of the target compound that can be produced per unit time and the volume of the reaction device.

$$STY[t_{nitrobenzene}(m^3_{reaction\ space} \cdot h)] = \text{amount produced } [t_{nitrobenzene}/h]/\text{reaction space}[m^3]$$

In the case of the nitration of benzene, the space-time yield is calculated as the quotient of the production of nitrobenzene in metric tonnes per hour and the volume of the reaction space. The reaction space is defined as the space which begins with the first dispersion of benzene and mixed acid and within which the reaction is completed to a degree of conversion of nitric acid of at least 99%. The reaction space is arranged in a technical device for carrying out chemical reactions, the reactor. In the simplest case, the reaction space is identical with the inside volume of the reactor. In this connection, the first dispersion means the first intensive mixing of benzene and mixed acid. This generally takes place either in a mixing nozzle or in a static mixing element. Simply combining a benzene stream and a mixed acid stream in a common feed pipe leading to the reactor, without taking particular measures to intensively mix the two streams, is not regarded as the first dispersion required in the present invention.

The residence time of the reaction mixture, consisting of the aromatic compound and the mixed acid, within the reaction space is the reaction time.

A high space-time yield is advantageous for the industrial application of a process because it makes it possible to construct compact reaction devices which are distinguished by a low investment volume per capacity.

With regard to the space-time yield of aromatic compound nitration, there is still a marked need for improvement over the prior art.

However, high space-time yields when carrying out a nitration adiabatically (in particular with a constant residence time in the reactor) inevitably lead to high temperature differences (adiabatic temperature jumps) between the start temperature (the temperature of the mixed starting materials before the start of the reaction, determined by calculating the combined temperature of the individual streams) and the reaction end temperature (the temperature after conversion of substantially all the nitric acid); and, as is clear from the prior art, high reaction end temperatures lead to an impairment of the selectivity. (See, e.g., EP 0 436 443 B1, column 15, l. 22-25).

SUMMARY OF THE INVENTION

It is an object of the present invention to provide a process for the adiabatic nitration of aromatic compounds, in which a high space-time yield is achieved without impairing the product quality.

It is also an object of the present invention to provide a continuous process for the production of nitrobenzene in compact reaction devices in which the nitrobenzene is obtained with high selectivity and in outstanding yields. These and other objects which will be apparent to those skilled in the art were achieved by the process for the preparation of nitrobenzene by adiabatic nitration of benzene with mixed acid containing sulfuric acid and nitric acid described more fully below.

DETAILED DESCRIPTION OF THE PRESENT INVENTION

The present invention is directed to a process for the preparation of nitrobenzene by adiabatic nitration of benzene with mixed acid containing sulfuric acid and nitric acid. In this process, benzene and mixed acid are introduced into a reactor either a) separately from one another or b) together, after they have been brought into contact with one another (i.e., in combination). When benzene and the mixed acid are introduced separately into the reactor, at least one of the benzene or mixed acid reactants is under a pressure, p1, on entry into the reactor. When the benzene and mixed acid have been brought into contact with one another prior to introduction into the reactor, the combined benzene and mixed acid are under a pressure, p1, on entry into the reactor. The benzene and mixed acid are then dispersed in one another in the reactor in from 1 to 30, preferably from 2 to 20, most preferably from 6 to 15, dispersing elements. Where more than one dispersing element is employed, the dispersing elements are arranged one behind the other. The benzene and nitric acid present in the mixed acid react to form nitrobenzene and nitrobenzene-containing reaction mixture is removed from the reactor. After leaving the reactor, the nitrobenzene-containing reaction mixture is subjected to a phase separation in a phase separation apparatus. In the gas phase of the phase separation apparatus, a pressure, p2, prevails. The pressure difference, i.e., p1−p2 is from 14 bar to 40 bar, preferably from 15 bar to 30 bar, more preferably from 15 bar to 25 bar, most preferably from 20 bar to 25 bar.

This process of the present invention makes it is possible to prepare large amounts of nitrobenzene in compact reactors with outstanding yields and selectivities.

In the first step of the process of the present invention, the reactants (i.e., benzene and mixed acid) are introduced into the reactor either a) separately from one another via different feed pipes or—preferably—b) after they have been brought into contact with one another, i.e., via a common feed pipe. In embodiment b), intensive mixing of the two streams does not yet take place during this first contact between benzene and mixed acid in the common feed pipe.

The pressure p1 on entry into the reactor is preferably measured in one of the respective feed pipes (benzene or mixed acid or common feed pipe for both) leading to the reactor.

Reactors according to the invention are preferably stirred tank, loop or tubular reactors. These can be arranged in series or in parallel. Combinations of different reactor types are also conceivable. Tubular reactors can be cylindrical or conical.

Dispersing elements useful in the process of the present invention are preferably sieve trays or perforated metal sheets.

Following the nitration reactor, the crude, liquid reaction product is preferably fed to a phase separation apparatus in which two liquid phases form, one being referred to as crude nitrobenzene (nitrobenzene and impurities) and the other as waste acid (substantially water and sulfuric acid). The crude nitrobenzene and the waste acid are worked up as described in greater detail below. At the same time as the two liquid phases form, gases escape from the liquid phase in the phase separation apparatus, so that the phase separation apparatus also has a third, gaseous phase.

The gas phase of the phase separation apparatus substantially contains nitrogen oxides as well as water vapor and benzene vapor. These gases are generally fed to a waste gas system. The pressure p2 is measured in this gas phase.

The present invention is explained in greater detail below.

According to the invention, benzene is nitrated with mixed acid. The mixed acid used contains preferably from 64% by mass to 71% by mass sulfuric acid and from 2% by mass to 8% by mass nitric acid; most preferably from 66% by mass to 69% by mass sulfuric acid and from 3% by mass to 5% by mass nitric acid, the remainder to 100% by mass preferably being water and the percentages by mass being based on the total mass of the mixed acid. The concentration of the sulfuric acid used is preferably from 65% by mass to 80% by mass and that of the nitric acid is preferably from 62% by mass to 70% by mass, in each case based on the total mass of the acid in question.

In the process of the present invention, benzene and mixed acid can be introduced into the nitration reactor separately from one another. It is preferred, however, for benzene to be metered into the mixed acid beforehand and for the two reactants to be passed into the reactor together. The ratio of the mixed acid stream (in mass of mixed acid added per hour) to the benzene stream (in mass of benzene added per hour) is also referred to as the phase ratio and is preferably from 12:1 to 30:1, more preferably from 12:1 to 18:1.

When benzene and mixed acid are metered into the reactor together, the pressure p1 is preferably measured in the common feed pipe leading to the reactor, preferably at a point immediately upstream of the reactor.

Alternatively, a pressure p1a can also be measured in the feed pipe for the mixed acid, before the benzene stream is combined with the mixed acid stream. The pressure p1a therein is identical with the pressure p1 on entry into the reactor, provided the nature of the metering of benzene into the mixed acid stream does not result in a pressure loss for the mixed acid stream. This is the case, for example, when benzene is introduced into the mixed acid stream using a lance or a mixing nozzle that preferably occupies only a small portion (preferably less than 10%) of the cross-sectional area of the mixed acid pipe. The pressure in the benzene feed pipe (p1b) upstream of the lance or mixing nozzle is preferably greater than the pressure p1a in the mixed acid feed pipe, more preferably from 0.5 bar to 10 bar greater.

If the manner of metering of the benzene into the mixed acid stream causes a significant pressure loss in the mixed acid stream, then it is preferred to measure the pressure p1 in the common feed pipe.

When benzene and mixed acid are fed separately into the reactor, it is preferred within the scope of this invention to measure the pressure p1 in the feed pipe for the mixed acid, preferably immediately upstream of the reactor, because this is more meaningful, as a result of the high phase ratio used for the adiabatic procedure, than a measurement in the feed pipe for the benzene stream.

Regardless of the precise manner in which benzene and mixed acid are fed (separately or together, with or without a mixing nozzle), the position of the relevant measuring site for determining the pressure p1 should be chosen so that the pressure of the relevant material stream (e.g., the process product obtained by bringing benzene and mixed acid into contact with one another or—in the case of separate feed—the mixed acid) on entry into the reactor can be determined correctly (i.e., there is either no significant pressure loss between the measurement site and the point at which the relevant material stream enters the reactor, or the pressure loss is known and can be taken into account in the calculation).

In the process according to the invention, the pressure measurement is conducted with any of the pressure measuring devices known to those skilled in the art, preferably using digital pressure transducers with a membrane manometer as sensor.

In the process according to the invention, the pressure difference between p1 and the pressure in the gas phase of the phase separation apparatus, p2, is from 14 bar to 40 bar, preferably from 15 bar to 30 bar, more preferably from 15 bar to 25 bar, most preferably from 20 bar to 25 bar, and is accordingly higher than hitherto conventional in the prior art.

In the present invention, the nitration reaction takes place in the reactor under adiabatic conditions, i.e., no technical measures are taken to supply heat to the reaction mixture or to remove heat from the reaction mixture. An important feature of the adiabatic nitration of aromatic hydrocarbons is that the temperature of the reaction mixture increases proportionally to the progress of the reaction, i.e., proportionally to the nitric acid conversion. A temperature difference is thereby obtained between the temperature of the mixed reactants, the aromatic compound and the mixed acid, before the start of the reaction (which is determined by thermodynamic calculations known to the person skilled in the art and is referred to below as the "start temperature") and the temperature of the reaction mixture after at least 99% nitric acid conversion (referred to below as the "reaction end temperature"). It is known to the person skilled in the art that the value referred to here as the start temperature is generally advantageously calculated as the combined temperature of the mixed acid and benzene streams, and the value referred to here as the reaction end temperature is preferably measured in the inlet of the phase separation apparatus. The difference between the start temperature and the reaction end temperature (the adiabatic temperature difference, also referred to below as $\Delta T_{adiabatic}$) depends on the nature of the nitrated hydrocarbon and on the ratio in which the mixed acid and the aromatic hydrocarbon are used. A low ratio of mixed acid and aromatic hydrocarbon (so-called phase ratio) gives a high adiabatic temperature difference and has the advantage that a large amount of the aromatic hydrocarbon is converted per unit time.

Under otherwise identical conditions, a higher value for $\Delta T_{adiabatic}$ indicates a more complete conversion. In the process of the present invention, the values for $\Delta T_{adiabatic}$ are preferably from 25 K to 60 K, most preferably from 30 K to 45 K. Despite the high adiabatic temperature difference, very good selectivities are achieved in the process of the present invention, which was not to be expected in view of the prior art.

The reaction end temperatures in the reactor are preferably from 120° C. to 160° C., most preferably from 130 to 140° C.

The process of the present invention is preferably carried out in a tubular reactor having a plurality of dispersing elements distributed over the length of the tubular reactor. These dispersing elements ensure intensive mixing and re-dispersion of benzene, nitric acid and sulfuric acid and water. Such a reactor, and the form of dispersing elements which can be used, are described, for example, in EP 0 708 076 B1 (FIG. 2) and EP 1 291 078 A2 (FIG. 1). The corresponding portions of these documents are hereby incorporated into the disclosure of the present invention.

A configuration for the tubular reactor as is described in EP 1 291 078 A2 (FIG. 1, paragraphs [0012] to [0013]) is most preferred. The corresponding portions of this document are hereby incorporated into the disclosure of the present invention. In EP 1 291 078 A2, from 3 to 11 dispersing elements made of tantalum are used (corresponding to 4 to 12 chambers; see paragraph [0012]). Each of these dispersing elements produces a pressure loss of from 0.5 bar to 4 bar and exhibits from 10 to 25 openings for a mass flow rate of 1 t/h. The openings can be slots, holes or bores. These parameters can likewise be implemented in the process of the present invention in order to avoid coalescence of the phases and keep the diameter of the organic droplets in the acid phase small. In EP 1 291 078 A2, the dispersing elements are designed so that the mean droplet diameter is less than 200 μm, most preferably less than 120 μM, and, as can be calculated by the person skilled in the art from the examples, a pressure of up to 10 bar is achieved in the enamelled steel reactor. In the process of the present invention, when a reactor configuration equivalent to that of EP 1 291 078 A2 is used, the dispersing elements are to be designed so that the absolute pressure upstream of the reactor is at least 15 bar, provided that the absolute pressure in the gas phase of the phase separation apparatus is less than or equal to 1.0 bar.

The dispersing elements preferably exhibit decreasing pressure losses in the direction of flow of the reactants. Most preferably, the second and every further dispersing element—in the direction of flow of the reactants—exhibits at most 80% of the pressure loss of the preceding dispersing element in each case.

In carrying out the process of the present invention, reactors having permissible absolute operating pressures of preferably at least 18 bar, most preferably at least 21 bar, are used. These reactors can be made, for example, of high-alloy steels. The resistance of suitable stainless steels under nitrating conditions is the result in particular of the fact that the nitric acid used for the nitration has a passivating effect. These reactors can also be made of enamelled steel. A combination of high-alloy and enamelled steels is also possible.

The liquid flowing through the dispersing elements causes the pressure of the liquid within the reactor to fall. This pressure drop allows modification of the configuration of the reactor so that the front section is constructed to withstand high operating pressures while the section in which the pressure is markedly lower can be constructed to withstand lower operating pressures.

Because steel enamel is a less expensive material compared with high-alloy steels, the use of steel enamel pipe segments for the whole of the structure of the tubular reactor is preferred, since this embodiment in particular achieves the aim of low investment costs. In order to be able to achieve absolute operating pressures of more than 15 bar in a reactor of enamelled steel, it may be necessary to make particular requirements of the quality of manufacture of the enamelled pipe segments that are to be used. Thus, for example, particular attention should be paid to the perpendicularity between the flange and the pipe. It may also be necessary to make particular demands of the enamelled flange face, in particular to remove uneven areas. An optimum contact surface for the gaskets can be obtained by grinding or polishing the enamelled flange face. In addition, uniform contact pressure can be achieved by suitable adjustment of the flange. In order to obtain the required permitted pressure, suitable gaskets should also be chosen. Suitable gaskets preferably cover the majority of the flange face and can optionally be centered between the flange faces by means of a binding. It is also possible to use gaskets which have been reinforced at the surfaces and the outside edges, for example, by means of glass fiber fabric on the surfaces or support rings on the outside edges.

After passing through the nitration reactor, the crude, liquid reaction product is fed to a phase separation apparatus. Any phase separation apparatus known to the person skilled in the art can be used. Preferably, the separation is carried out in a gravity separator. The liquid phases, crude nitrobenzene and waste acid, obtained in the phase separation apparatus are preferably worked up as described below.

The waste acid is usually fed to a flash evaporator in which, during decompression of the waste acid to a reduced pressure range, water vaporizes and the waste acid is thus cooled and concentrated. The adiabatic procedure for the nitration of benzene with mixed acid has the advantage that the heat of reaction of the exothermic reaction is used to heat the waste acid so greatly that at the same time the concentration and the temperature that the sulfuric acid exhibited prior to mixing with nitric acid and benzene can be established again in the flash evaporator.

The crude nitrobenzene obtained in the phase separation apparatus still contains sulfuric acid, water, benzene as well as nitrophenols and dinitrobenzene as impurities. These impurities are separated off by suitable working-up processes, e.g., washing and distillation steps. A possible form of this working up is described in EP 1 816 117 A1 (paragraph [0006]). The corresponding sections of EP 1 816 117 A1 are hereby incorporated into the disclosure of the present invention. Other forms are also possible, however.

The gases formed in the phase separation apparatus are preferably fed to a waste gas system.

By the process according to the invention, a space-time yield of preferably more than 7.0 t of nitrobenzene per cubic meter volume of the reaction space per hour is achievable with a very low content of by-products. The low content of by-products despite large adiabatic temperature differences—as a result of the high space-time yields—is made possible by the use of high pressure (i.e., from 14 to 40 bar above the pressure in the gas phase of the phase separation apparatus upstream of the reactor).

The process according to the invention has been described herein using the example of nitrobenzene. However, the person skilled in the art can readily extend the invention to the preparation of other nitoaromatic compounds; for example, to the preparation of dinitrotoluene by nitration of toluene.

Having thus described the invention, the following Examples are given as being illustrative thereof.

EXAMPLES

Examples 1 to 3 (not According to the Invention), Example 4 (According to the Invention)

The examples below were carried out under the following conditions:

All the tests were carried out in a tubular reactor of enamelled steel having an inside volume of 455 ml. The tubular reactor was mounted vertically, and flow was from the bottom. The tubular reactor contained 10 dispersing elements made of tantalum, which exhibited decreasing pressure losses from top to bottom. The pressure prevailing in the mixed acid (p1a) was measured upstream of the tubular reactor using a membrane manometer, before benzene was introduced into the mixed acid by means of a low-pressure-loss lance and the resulting stream was introduced into the reactor. In the present test arrangement, p1a can be equated with the pressure p1 of the process product obtained by bringing benzene and mixed acid into contact on entry into the reactor. The sulfuric acid always had a concentration of 71% by mass and the nitric acid always had a concentration of 69.2% by mass. The mixed acid always had a temperature of 96° C., and the benzene was preheated and always had a temperature of 80° C. The purity of the benzene was always more than 99% by mass. After passing through the reactor, the crude reaction product was introduced into a static phase separation apparatus operated without pressure.

The amount of benzene indicated in Table 1 was reacted with the mixture of the indicated amounts of nitric acid and sulfuric acid. The benzene excess, based on the product nitrobenzene, was in each case 6% by mass.

At the end of the tubular reactor, the adiabatic end temperature was measured and the adiabatic temperature difference $\Delta T_{adiabatic}$ was calculated by means of the combined temperature of the mixed acid and benzene streams. The nitrobenzene separated from acid in the phase separation apparatus was analyzed to determine the dinitrobenzene and nitrophenols contents. From the group of nitrophenols, picric acid can be identified separately. In all the tests, the nitric acid used was reacted completely (>99.99% according to ion chromatography analysis of the waste acid for nitrate). In Example 4 (according to the invention), it was possible with a pressure difference of 15.8 bar to achieve a space-time yield of more than 7.0 $t_{nitrobenzene}/(m^3_{reaction\ space} \cdot h)$ and, despite the high adiabatic temperature difference, the lowest contents of by-products.

TABLE 1

Parameters and results of Examples 1 to 4.

| Example: | 1* | 2* | 3* | 4 |
|---|---|---|---|---|
| Space-time yield[1] | 5.5 | 6.2 | 6.4 | 7.2 |
| HNO$_3$ stream [g/h] | 1864 | 2089 | 2169 | 2410 |
| H$_2$SO$_4$ stream [g/h] | 30000 | 34000 | 34000 | 38000 |
| Benzene stream [g/h] | 1760 | 1970 | 2050 | 2275 |
| Absolute pressure on entry into the reactor (p1) [bar] | 10.7 | 13.4 | 13.6 | 16.8 |
| Absolute pressure in the gas phase of the phase separation apparatus (p2) [bar] | 1.0 | 1.0 | 1.0 | 1.0 |
| Pressure difference p1 – p2 [bar] | 9.7 | 12.4 | 12.6 | 15.8 |
| $\Delta T_{adiabatic}$ [K] | 42.3 | 41.7 | 44.4 | 44.1 |
| Nitric acid conversion [%] | >99.99 | >99.99 | >99.99 | >99.99 |
| Dinitrobenzene content [ppm by mass] | 293 | 211 | 213 | 176 |
| Nitrophenol content (total) [ppm by mass] | 2153 | 2169 | 2055 | 1973 |
| Picric acid content [ppm by mass] | 171 | 136 | 122 | 89 |

*Comparative Example
[1]Space-time yield = $[t_{nitrobenzene}/(m^3_{reaction\ space} \cdot h)]$ Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of nitrobenzene by adiabatic nitration of benzene with a mixed acid comprising sulfuric acid and nitric acid, the process comprising:
  (i) introducing the benzene and the mixed acid into a reactor either
    a) separately with at least one of the benzene or the mixed acid being under a pressure p1 on entry into the reactor
    or
    b) together, after being brought into contact with one another, under a pressure p1 on entry into the reactor,
  (ii) dispersing the benzene and the mixed acid in one another in the reactor with from 1 to 30 dispersing elements, provided that when more than one dispersing element is present, the dispersing elements are arranged one behind the other,
  (iii) removing reaction product from the reactor,
  (iv) subjecting the reaction product removed in (iii) to a phase separation in a phase separation apparatus, in which a gas phase pressure p2 prevails
in which
p1−p2=from 14 bar to 40 bar.

2. The process of claim 1 in which the reactor temperature after at least 99% conversion of nitric acid minus the combined benzene and mixed acid reactants' temperature before start of the nitration reaction is from 25 K to 60 K.

3. The process of claim 1 in which from 2 to 20 dispersing elements are used in (ii).

4. The process of claim 3 in which each dispersing element exhibits a pressure loss, and the pressure losses of the dispersing elements decrease in the direction of flow of the benzene and mixed acid reactants.

5. The process of claim 4 in which the second and each subsequent dispersing element in the direction of flow of the reactants exhibits at most 80% of the pressure loss of the preceding dispersing element.

* * * * *